United States Patent [19]

Hudson

[11] Patent Number: 4,577,047

[45] Date of Patent: Mar. 18, 1986

[54] CATALYSTS AND PROCESS FOR THE SELECTIVE HYDROGENATION OF ACETYLENES

[75] Inventor: Henry C. Hudson, New Caney, Tex.

[73] Assignee: Shell Oil Company, Houston, Tex.

[21] Appl. No.: 768,287

[22] Filed: Aug. 22, 1985

Related U.S. Application Data

[62] Division of Ser. No. 675,175, Nov. 27, 1984, Pat. No. 4,551,443.

[51] Int. Cl.[4] ................................................ C07C 5/03
[52] U.S. Cl. .................................... 585/260; 585/259
[58] Field of Search ........................................ 585/260

[56] References Cited

U.S. PATENT DOCUMENTS

| | | | |
|---|---|---|---|
| 2,946,829 | 7/1960 | Likins et al. | 585/260 |
| 3,098,882 | 7/1963 | Arnold | 585/259 |
| 3,113,980 | 12/1963 | Robinson | 585/260 |
| 3,116,342 | 12/1963 | Robinson et al. | 585/260 |
| 4,038,175 | 7/1977 | Bhasin | 208/144 |
| 4,119,567 | 10/1978 | Bartsch | 252/430 |
| 4,126,645 | 11/1978 | Collins | 585/260 |
| 4,230,897 | 10/1980 | Cosyns et al. | 585/260 |

Primary Examiner—Curtis R. Davis

[57] ABSTRACT

This invention relates to a catalyst containing palladium and optionally chromium on an alumina which is used for the selective hydrogenation of acetylenic hydrocarbons in olefin gas streams. The catalyst is characterized by the use of an alumina support having a surface area of less than about 5 square meters per gram, a Hg pore volume of between about 0.2 and about 0.5 cubic centimeters per gram and wherein at least 40% of the pore volume is contained in pores having pore diameters of greater than about 10 microns.

28 Claims, 9 Drawing Figures

CATALYSTS AND PROCESS FOR THE SELECTIVE HYDROGENATION OF ACETYLENES

This is a division of application Ser. No. 675,175, filed Nov. 27, 1984, and now U.S. Pat. No. 4,551,443.

FIELD OF THE INVENTION

This invention relates to palladium on alumina catalysts and their use in the selective hydrogenation of acetylenic compounds in olefin streams.

BACKGROUND OF THE INVENTION

Palladium is a particularly useful metal for hydrogenation reactions. It has been utilized supported on various porous oxides substrates for the selective hydrogenation of acetylenic compounds in olefins streams without the concurrent hydrogenation of the olefins. However, when these catalysts have been used commercially, certain problems have arisen. The selectivity for the hydrogenation of the acetylene rather than the olefins is never 100%, with a certain fraction of the olefins being converted to saturated hydrocarbons. Frequently, it is desired to convert the acetylenic materials to olefins, and a highly reactive hydrogenation catalyst that would take the reaction on through to the saturated hydrocarbon would not be desirable. Olefins frequently have a higher economical value than the saturated hydrocarbons, which in many commercial applications would be utilized only for their fuel value.

U.S. Pat. No. 3,098,882, issued July 23, 1963, generally discloses the use of a palladium-chromium catalyst supported on a alumina for the selective hydrogenation of acetylene. This reference broadly discloses aluminas as supports, but does not particularly point out any special alumina as having preferred properties.

Many special forms of alumina have been utilized in order to obtain enhanced properties of the resultant catalyst. U.S. Pat. No. 4,038,175, issued July 26, 1977, discloses a palladium on an alpha-alumina support for the hydrogenation of dripolenes which are liquid unsaturated hydrocarbon by-products of a hydrocarbon cracking process for the production of ethylene. The disclosure of the support is a broad generic disclosure of low surface area alpha-alumina supports which have the following characteristics: (a) a porosity of 0.1–0.8 cc/gm; (b) a surface area of 0.1–10 $m^2/g$; and (c) an average pore size of 0.05–100 microns with a major portion of the pores having a pore size in the range of 0.05–10 microns.

U.S. Pat. No. 4,119,567, issued Oct. 10, 1978, discloses palladium supported on an alpha alumina support having a crystalline alpha-alumina content of greater than 96%, a surface area of 2–6 $m^2/g$, an average crush strength of 20–45 lbs, and a bulk density of less than 1.35 cc/g. The catalyst is disclosed as useful for the preparation of unsaturated organic esters such as vinyl and allyl acetate.

In U.S. Pat. No. 2,946,829, issued July 26, 1960, a palladium catalyst supported on an alumina carrier is disclosed wherein the alumina carrier is characterized by a pore volume of surface pores having a threshold diameter not greater than 800 Å in the range from 0 to 0.4 cc/g, and further characterized in that the palladium is predominately concentrated in the external portion of the carrier.

In U.S. Pat. No. 3,113,980, issued Dec. 10, 1963, there is disclosed a palladium catalyst supported on an alumina whose pores have a mean radius in the range of 100 to 1400 Å units and which has a surface area in the range of 5 to 32 $m^2/g$.

In U.S. Pat. No. 3,116,342, issued Dec. 31, 1963, there is disclosed a palladium catalyst supported on an alumina which has pores of a mean radius of at least 100 Å and not more than 1400 Å and which catalyst support has a surface area in the range of 5 to 65 $m^2/g$.

In U.S. Pat. No. 4,126,645, issued Nov. 21, 1978, there is disclosed a palladium catalyst supported on particulate alumina having a surface area in the range of 5 to 50 $m^2/g$, a helium density under 5 $g/cm^3$, a mercury density of under 1.4 $g/cm^3$ and a pore volume of at least 0.4 $cm^3/g$, at least 0.1 $cm^3/g$ of which is in the pores of radius over 300 Å units, the palladium being present in the region of the catalyst particles not more than 150 microns beneath their geometric surface.

In U.S. Pat. No. 4,230,897, issued Oct. 28, 1980, there is disclosed a process for hydrogenating acetylenic hydrocarbons found in diolefinic-containing hydrocarbon streams, said hydrogenation being carried out at least partially in the liquid phase, and wherein a palladium on alumina catalyst is utilized, improvement being in this instance of utilizing the palladium on alumina catalyst wherein the average size of the palladium crystallites in said catalyst is at least 50 Å.

None of the references discussed herein specifically disclose the use in a catalyst of applicant's supports. The use of these supports in catalysts for the selective hydrogenation of acetylenic impurities in olefin streams provides advantages such as improved selectivities and longer periods of use before regeneration.

SUMMARY OF THE INVENTION

This invention relates to a supported palladium catalyst optionally containing chromium which provides for improved selectivities and longer periods of use prior to regeneration in the selective hydrogenation of acetylenic impurities in olefinic hydrocarbons streams. This invention utilizes a unique support which contributes to these advantages. The support comprises alumina with a surface area of less than about 5 $m^2/g$, a pore volume (Hg) of between 0.2 and about 0.5 cc/g and wherein greater than about 40% of the pore volume is contained in pores having diameters greater than about 10 microns.

BRIEF DESCRIPTION OF DRAWINGS

FIG. 2, B), supports not according to the instant invention (FIG. 3, C; FIG. 4, D) and a commercial palladium-aluminum catalyst (FIG. 5, C31-1A).

DESCRIPTION OF THE PREFERRED EMBODIMENTS

The instant invention comprises a process for selectively hydrogenating acetylenic hydrocarbon impurities found in olefin-containing hydrocarbon streams. The catalyst utilized for this selective hydrogenation is palladium, optionally with chromium, supported on an alumina support wherein the improvement comprises utilizing as the support a porous oxide material comprising an alumina having a surface area less than about 5 $m^2/g$, a pore volume (Hg @ 3000 psi) of between about 0.2 to about 0.5 cc/g and wherein at least 40% of the pore volume is contained in pores having pore diameters of greater than about 10 microns.

The palladium concentrations in the catalyst are not critical but will typically range from about 0.001 to about 5% by weight based on the metal, and preferably from about 0.01 to about 0.5% by weight. Lesser amounts of palladium than 0.001% by weight can be utilized. However, at some point the activity of the catalyst is not sufficiently high to be commercially useful. By the same token amounts greater than 5% by weight of palladium can be utilized. However, due to the high cost of palladium, such high usages of palladium normally cannot be justified.

The catalyst optionally contains chromium. The catalyst without the presence of chromium is a useful catalyst. However, the addition of the chromium to the catalyst is believed to provide a longer life for the catalyst. When chromium is present, it is preferably found present in the weight ratio of palladium to chromium ranging from about 2:1 to about 1:2. In most instances, it is preferred that the weight ratio of palladium to chromium be approximately unity. The chromium concentrations will typically range from about 0.001 to about 5% by weight based on the metal, and preferably from about 0.01 to about 0.5% by weight. Although concentration ranges are given here on the basis of the metal, it is believed that most of the chromium is present in the final catalyst in the form of an oxide.

Figure 1:
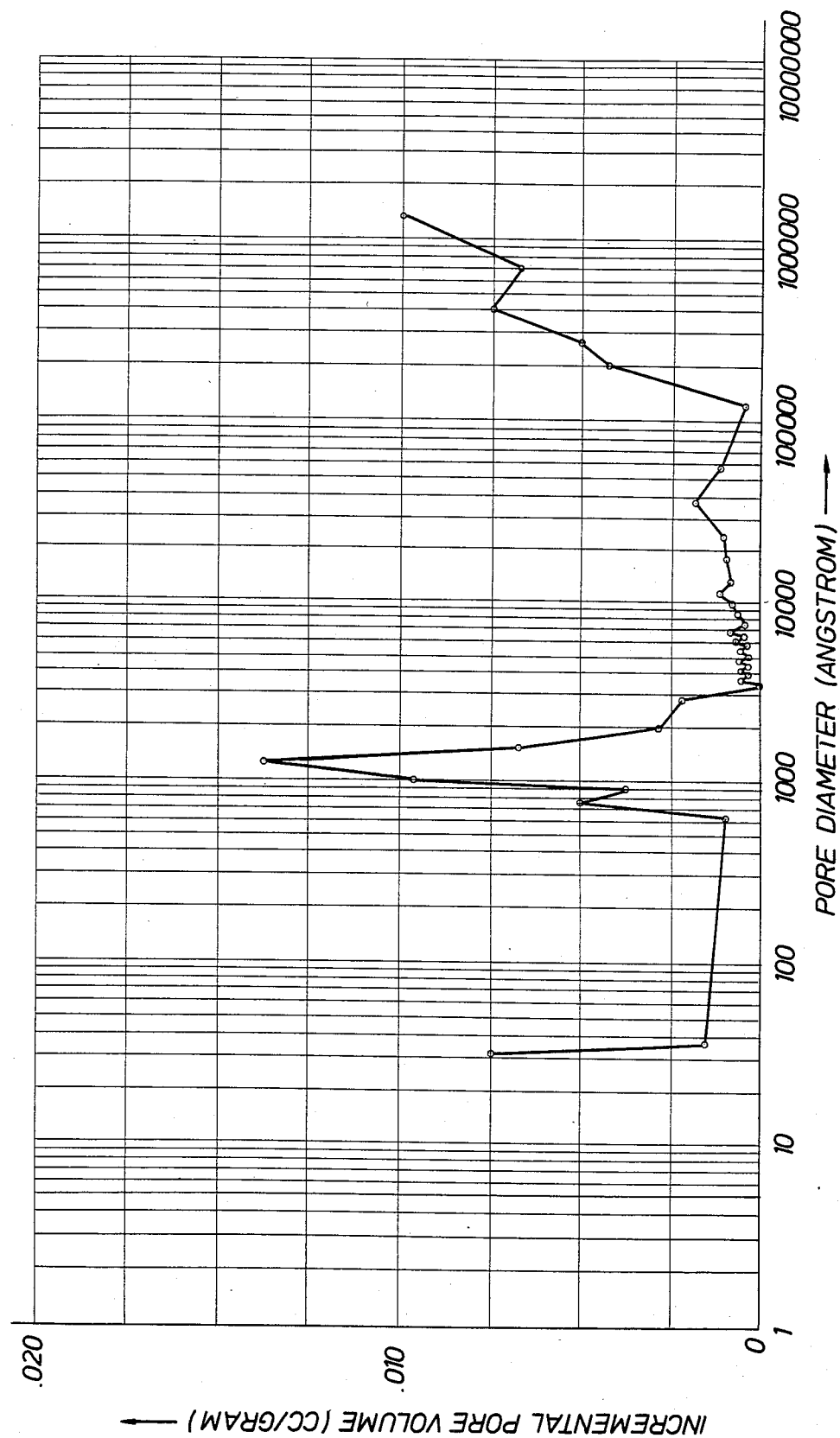
FIGS. 1–5 are plots of incremental pore volume versus pore diameter for supports used in the instant invention (FIG. 1, A.
Figure 2:
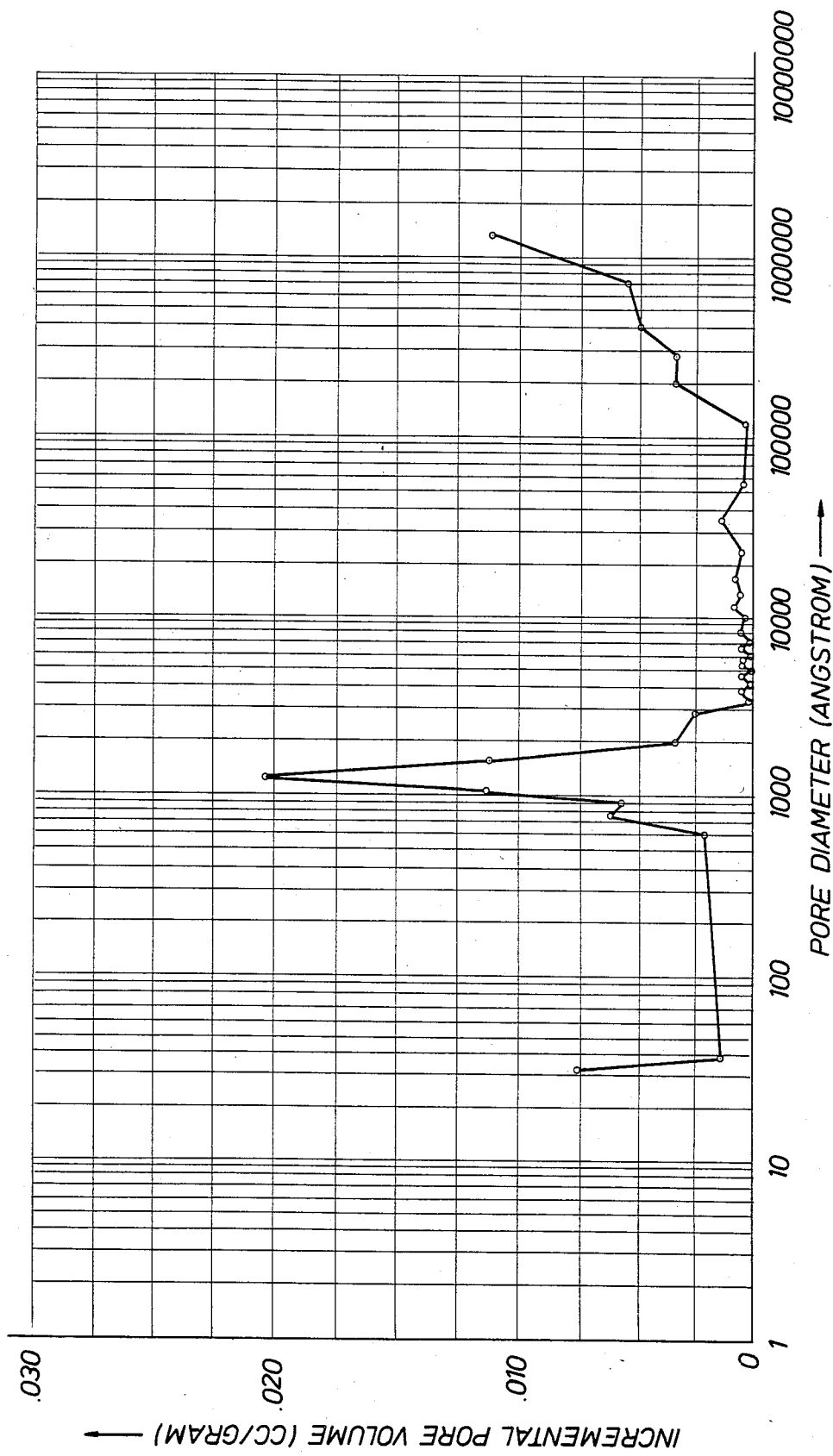

The unique carrier utilized in the catalyst of the instant invention is believed to be primarily responsible for the extension of the time period that the catalyst can be used before it must be regenerated as well as its high selectivity as a function of time. The carrier comprises basically a porous alumina support. The support will thus contain at least 50%, preferably about 90%, by weight of alumina, preferably alpha alumina. Minor amounts of other materials such as, for example, those shown in Table I, can be present in the support without being detrimental. For example, a relatively high percentage of silica, say up to about 10% has been found to be very useful in this support. The alumina will be present in the catalyst support primarily in the so-called alpha phase. Small amounts of other phases such as gamma, eta, etc. may be present. The use of the alpha alumina provides for supports that have relatively low surface areas. Typically, the surface areas are less than about 5 $m^2/g$, preferably less than about 5 $m^2/g$ and greater than about 0.5 $m^2/g$, more preferably ranging between about 1.5 to about 4.5 $m^2/g$. Surface areas are measured by the so-called "BET Method" (Brunauer, Emmett and Teller). The pore diameters are determined by mercury intrusion up to 3000 psi and calculated using a contact angle of 130° and a mercury surface tension of 0.473N/m. The median pore diameter (Hg intrusion) ranges from about 0.5 to about 30 microns, preferably from about 1 to about 25 microns. The pore volume (Hg) is measured by mercury intrusion at 3000 psi and in the instant catalyst ranges from about 0.1 to about 0.8, preferably from about 0.2 to about 0.5 cc/g. The critical aspect of this invention involves utilization of supports which have greater than about 40% and more preferably greater than about 50% (a major proportion) of their pore volume contained in pores having pore diameters greater than about 10 microns. It has been found that the use of these unique carriers results in catalysts that can be used for much longer periods of time prior to regeneration. Typical specifications for supports found useful in the instant invention are given in Table I below. Typical pore distribution curves for supports A and B listed in Table I below are shown in FIGS. 1 and 2, respectively.

TABLE 1
TYPICAL CARRIER PROPERTIES

| Carrier | A | B |
| --- | --- | --- |
| Surface Area $m^2/g^a$ | 2.0 | 3.8 |
| Cold Water Absorption, cc/gm$^b$ | 0.24 | 0.25 |
| Hot Water Absorption cc/gm$^c$ | 0.37 | 0.47 |
| Compacted Bulk Density, g/cc$^d$ | 0.80 | 0.64 |
| Crushing Strength, FPCS, lbs$^e$ | 18 | 10 |
| Total Pore Volume, Hg, cc/g$^f$ | 0.34 | 0.45 |
| Median Pore Diameter, Microns$^f$ | 18 | 10 |
| Percent Pore Volume in Pores of Greater Than 10 Microns in Diameter$^f$ | 55 | 46 |
| $Al_2O_3$, wt % | 93.2 | about 93 |
| Alumina Phase | Alpha | Alpha |
| $S_iO_2$, wt % | 6.0 | about 6 |
| $Na_2O$, wt % | 0.2 | — |
| $Fe_2O_3$, wt % | 0.2 | — |
| TiO, wt % | 0.2 | — |
| CaO, wt % | 0.1 | — |
| MgO, wt % | 0.1 | — |

$^a$BET, (Krypton) Micromeritics Digisorb 2500 Instrument.
$^b$A weighed quantity of carrier is soaked in $H_2O$ at 70° F./1 atmos. for 1 hr., excess $H_2O$ removed, then re-weighed.
$^c$A weighed quantity of carrier is soaked in boiling $H_2O$ 30 min., cooled, excess $H_2O$ removed, then re-weighed.
$^d$200 ml. fully settled in a graduate and weighed.
$^e$Flat plate, single pellet, ¼" diameter ring - ¼" long - 0.1" bore.
$^f$Determined by mercury intrusion, to 3000 psi using a Autopore 9200, manufactured by Micromeritics Instrument Corporation (130° contact angle, 0.473 N/m surface tension of Hg).

The catalyst is prepared in typical fashion utilizing solutions of palladium salts optionally containing salts of chromium to impregnate the porous alumina support. Preferably, the impregnating solution will be an aqueous solution of a soluble palladium salt such as, for example, palladium nitrate and optionally a soluble chromium salt such as, for example, chromium nitrate. Suitable organic solvents can be utilized when the metals used are organo-metallics such as palladium acetylacetonate. The catalyst is prepared by spraying, dipping or otherwise applying the solution of the palladium salt, optionally containing the chromium salt, to the alumina carrier. The palladium salt and the chromium salt, when utilized, may be applied from the same solution or separate solutions. The solution of catalytic metals may be applied to the support one time to get the desired concentration, or alternatively the solution may be applied several times. For example, the carrier may be impregnated, dried and/or calcined, reimpregnated, dried, etc. The preferred impregnation technique is the so-called "dry impregnation" technique. In this technique that amount of impregnating solution is utilized that will just fill the pore volume of the catalyst. The catalyst is then impregnated with the solution by spraying, dipping, or otherwise mixing the solution with catalyst support.

After the impregnation, the catalyst is typically dried to remove the water of solution. Drying will typically range in temperatures from about 25° C. to about 200° C. when water is used as a solvent. Drying may be carried out in air, under forced draft, under vacuum or by use of other traditional methods. When drying to remove water is carried out in an air oven, typically the drying temperature will range from about 120° to about 170° C. After drying the catalyst is typically calcined in air at temperatures ranging from about 500° C. to about 1000° C., preferably from about 700° to about 900° C.

After drying, the catalyst is typically calcined in order to decompose the metal salts. If the catalyst contains chromium and the catalyst is to be utilized in an environment containing water, it is desirable to calcine the catalyst at a temperature ranging between about 750° C. to about 900° C., more preferably between about 750° C. to about 850° C. and most preferably between about 800° C. to about 840° C. It is found that the more elevated temperature utilized for the calcining of catalysts containing chromium converts a significant portion of the chromium salt to chromium oxide wherein the chromium is predominately in the water insoluble +3 state. When lesser calcining conditions are utilized, it is possible that the chromium could be in the water soluble +6 oxidation state, and contact of the catalyst with water could adversely affect its properties.

After calcining, the catalyst is preferably treated with hydrogen to effect the reduction of the palladium oxide to palladium metal. It is possible, however, to use the catalyst without further treatment. Reduction of the palladium would then gradually take place under the reducing conditions found in the reaction process for the selective hydrogenation of the acetylene. As used herein the term "catalyst" refers to palladium- and optionally chromium-containing supported materials both before reduction or after.

The catalysts of the instant invention are particularly designed for selectively hydrogenating acetylenic hydrocarbon impurities in olefinic streams. Typically, the acetylenic impurities will be less than about 5% by weight of the total olefin stream, more typically they will be less than about 2% by weight of the olefin stream. The olefinic stream is typically comprised of the lower olefin materials having carbon numbers ranging from about 2 to about 4, for example, ethylene, propylene, and butenes. These olefinic streams may contain a minor portion, say, less than 50%, of saturated hydrocarbons. Hydrogen as well as small amounts of carbon monoxide may also be present in the olefin stream. Two broad classes of olefin streams are found in commercial operations. One type contains larger amounts of hydrogen, methane and ethane. A typical process stream of this type may comprise about 25% hydrogen, 10% methane, 0.3% acetylene, 40% ethylene and 25% ethane. Another type of stream has been processed to removed a substantial portion of the hydrogen and methane (demethanized). A typical process stream of this type comprises about 80% ethylene, 20% ethane and about 0.7% acetylene.

The acetylenic hydrocarbon impurities to be selectively hydrogenated in the instant process are the lower acetylenic hydrocarbons, for example, acetylene, methyl acetylene, dimethyl acetylene, ethyl acetylene, etc. Acetylene is the preferred species to be removed by the use of the instant catalyst.

In use, the catalyst of the instant invention is contacted with the acetylenic hydrocarbon-containing olefinic stream at temperatures ranging from about 50° C. to about 200° C. and at pressures ranging from about 50 to about 500 psig. The gaseous hourly space velocity utilized will range from about 50 to about 10,000. Hydrogen may be added to the gaseous hydrocarbon stream if not already present. It is necessary that the molar ratio of hydrogen to acetylenic hydrocarbon be at least 1.0 in order to effect substantially complete removal of the acetylenic impurity. It is understood that when the instant catalyst is utilized in multistage reactors, the molar ratio of hydrogen to acetylenic hydrocarbon impurity in any one reactor may be less than 1.0 but that when the entire reactor scheme is considered, the molar ratio of hydrogen present and/or added to the acetylenic hydrocarbon impurity to be removed is at least 1.0. When hydrogen is added because of a lack of hydrogen in the feed stream, hydrogen will be typically added in a mole ratio to acetylenic hydrocarbon impurity ranging from 1.0 to about 2.0.

The olefin stream is contacted with the catalyst in the gaseous state or in a mixed gas-liquid state, depending upon the types of olefins present. When ethylene is the primary olefin present, contact will be primarily in the gaseous states. As more and more higher olefins, such as $C_3^=$, $C_4^=$, $C_5^=$, etc, are present, the state of the olefin stream will be shifted more to the liquid.

The selectivity and activity of the instant catalysts will gradually decline over a period of time due to deposition of carbonaceous material on the catalysts. While these catalysts decline more slowly than traditional catalysts they can quite suitably be regenerated for a number of cycles in order to restore them to substantially their initial activity and selectivity. The instant catalysts are suitably regenerated by contact with steam/air mixtures at elevated temperatures ranging from about 300° C. to about 450° C.

The catalysts of the instant invention, the process for preparing them, and their use for the selective hydrogenation of acetylenic hydrocarbons in olefinic hydrocarbon streams will be further described below by the following illustrative embodiments which are provided for illustration and are not to be construed as limiting the invention.

Catalyst Preparation

EXAMPLE I

A palladium impregnating solution was prepared by adding water to aqueous palladium nitrate solution sufficient to make a volume of 24 milliters. 24 Milliters corresponds to the water pore volume of 100 grams of carrier A listed in Table I. The impregnating solution contained 0.05 grams of palladium. 100 Grams of carrier A was placed in a round bottom flask equipped with a stopper and the impregnating solution was added to the alumina in increments while rotating the flask. After the alumina was impregnated, the wet alumina was allowed to set for about 15 minutes with the stopper in place. The impregnated alumina was then transferred to a quartz evaporating dish and placed in an oven under an air flow. The temperature of the oven was maintained at about 150° C. for about 2 hours in order to dry the catalyst. The temperature was then raised to about 816° C. (1500° F.) and held at that temperature for about one hour in order to calcine the catalyst. The catalyst was then removed from the oven and allowed to cool to ambient conditions in a desiccator.

EXAMPLE II

An impregnating solution was made up utilizing palladium nitrate and chromium nitrate in sufficient water to correspond to the water pore volume of carrier A in Table I. The impregnating solution contained 0.05 grams of palladium and 0.05 grams of chromium, measured as the metal. 100 Grams of the most preferred carrier A was placed in a round bottom flask equipped with a stopper and the impregnating solution was added to the alumina in increments while rotating the flask. When the alumina was impregnated, the wet alumina was allowed to set for about 15 minutes with the stopper in place. The impregnated alumina was then transferred to a quartz evaporating dish and placed in an oven under an air flow. The temperature of the oven was maintained at about 150° C. (300° F.) for about two hours in order to dry the catalyst. The temperature was then raised to about 816° C. (1500° F.) and held at that temperature for about one hour in order to calcine the catalyst. The catalyst was removed from the oven and allowed to cool to ambient temperature in a desiccator.

EXAMPLE III

This example is similar to Example II above; however, in this example a different impregnating technique is utilized. An impregnating solution is again made up of palladium nitrate and chromium nitrate in an amount equivalent to the water pore volume of carrier A and which solution contains sufficient palladium and chromium to provide 0.05% by weight of palladium and 0.05% by weight of chromium in the final catalyst. To impregnate the carrier the impregnation solution is sprayed on the carrier which is being tumbled in an impregnation vessel. After all the impregnation solution has been sprayed on the carrier the tumbling is continued for an additional hour. The impregnated carrier is then transferred to a rotating kiln where it is calcined for a residence time of about an hour at a catalyst bed outlet temperature of about 1500° to about 1550° F. (816°-843° C.).

EXAMPLE IV

The preparative technique of Example II is repeated utilizing as a carrier the carrier B which is listed in Table I.

EXAMPLE N-1

Figure 3:
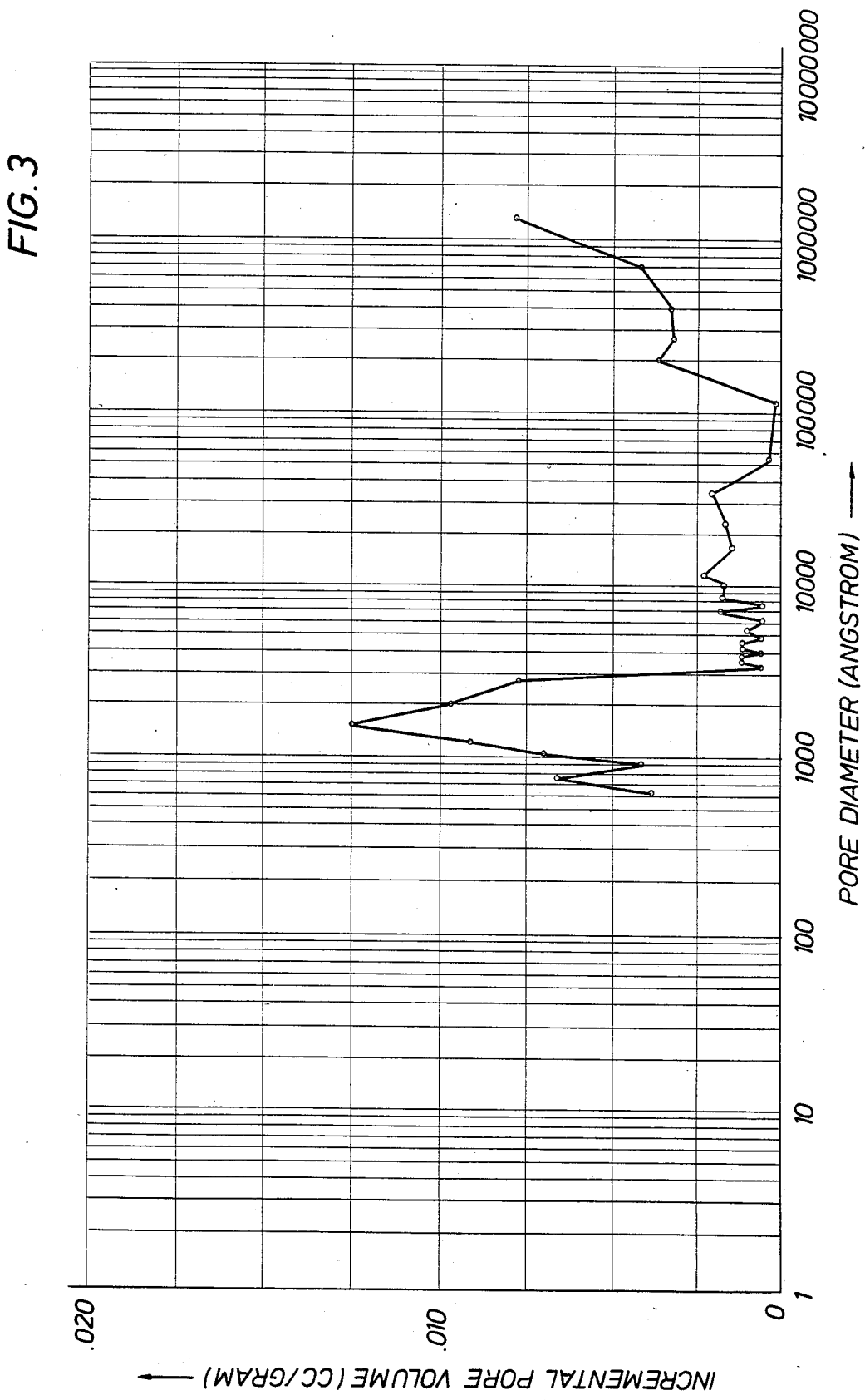

A catalyst not according to this invention was prepared utilizing the technique of Example II above using as a carrier the carrier C listed in Table II below. The pore distribution characteristics of carrier C are given in FIG. 3.

EXAMPLE N-2

Figure 4:
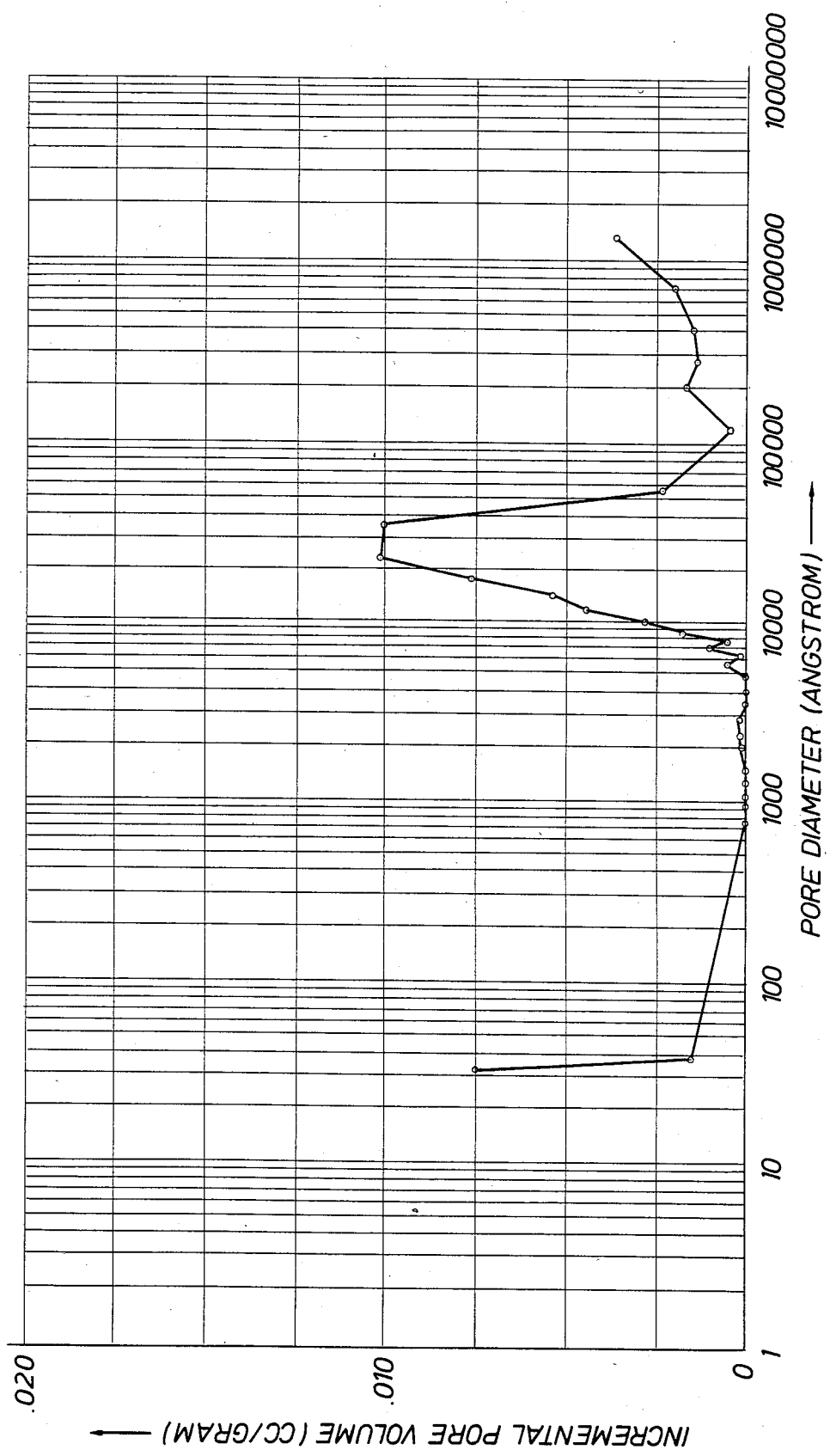

A catalyst not according to this invention is prepared in the fashion similar to Example II above using as a carrier the carrier D listed in Table II below. The pore volume characteristics of catalyst D are given in FIG. 4.

TABLE II

| Carrier | Carriers C & D | | |
|---|---|---|---|
| | C | D | C31-1A |
| Surface Area m²/g | 6.2 | 0.4 | 50 |
| Total Pore Vol(Hg) cc/g | 0.346 | 0.241 | 0.358 |
| Median Pore Diameter, microns | 6.0 | 4.2 | 0.32 |
| % Pore Volume in Pores of Greater than 10 microns in Diameter | 34.0 | 25.4 | 11.3 |
| Al₂O₃ Phase | Alpha | Alpha | primarily Alpha |
| Al₂O₃, wt % | About 93 | About 93 | — |
| SiO₂, wt % | About 6 | About 6 | — |

Process for Selectively Hydrogenating Acetylene in an Olefin Stream

The following example illustrates the general technique which is utilized to test the catalysts of the instant invention as well as the comparative catalysts for the selective hydrogenation of acetylene.

20 Cubic centimeters of catalyst (whole pellet, nominal ¼"×¼"–0.1" bore rings) are placed in a microreactor which consists of an 18" length of ¾" stainless steel tubing which is cast into an aluminum block and electrically compensated for essentially isothermal temperature control. The catalyst in its calcined or oxidized form, is activated by hydrogen reduction at one atmosphere for two hours at 400° F. (204° C.) using a hydrogen rate of about 2 cubic feet per hour.

After the prereduction is completed and the temperature has been lowered to 125° F. the reactor is pressured up to 300 lbs. by using hydrogen pressure to 125 lbs. gauge pressure and then using feed gas to pressure the rest of the way to 300 lbs. gauge pressure. The feed gas comprises 99% ethylene and 1% acetylene. A feed gas flow rate of 23 liters per hour is initiated by establishing a given pressure drop across a calibrated capillary, and hydrogen is added in the same manner at a rate to produce a hydrogen to acetylene mol ratio of about 1.0.

The acetylene conversion is monitored by gas chromatographic analysis of the reactor effluent. A conversion level of 80% of the acetylene is maintained to simulate the first stage of a two-stage reactor unit. The reactor temperature or hydrogen input is varied in order to maintain the acetylene conversion level at 80%. The catalyst selectivity is defined as the percent of acetylene converted that shows up as a net ethylene make.

Figure 5:
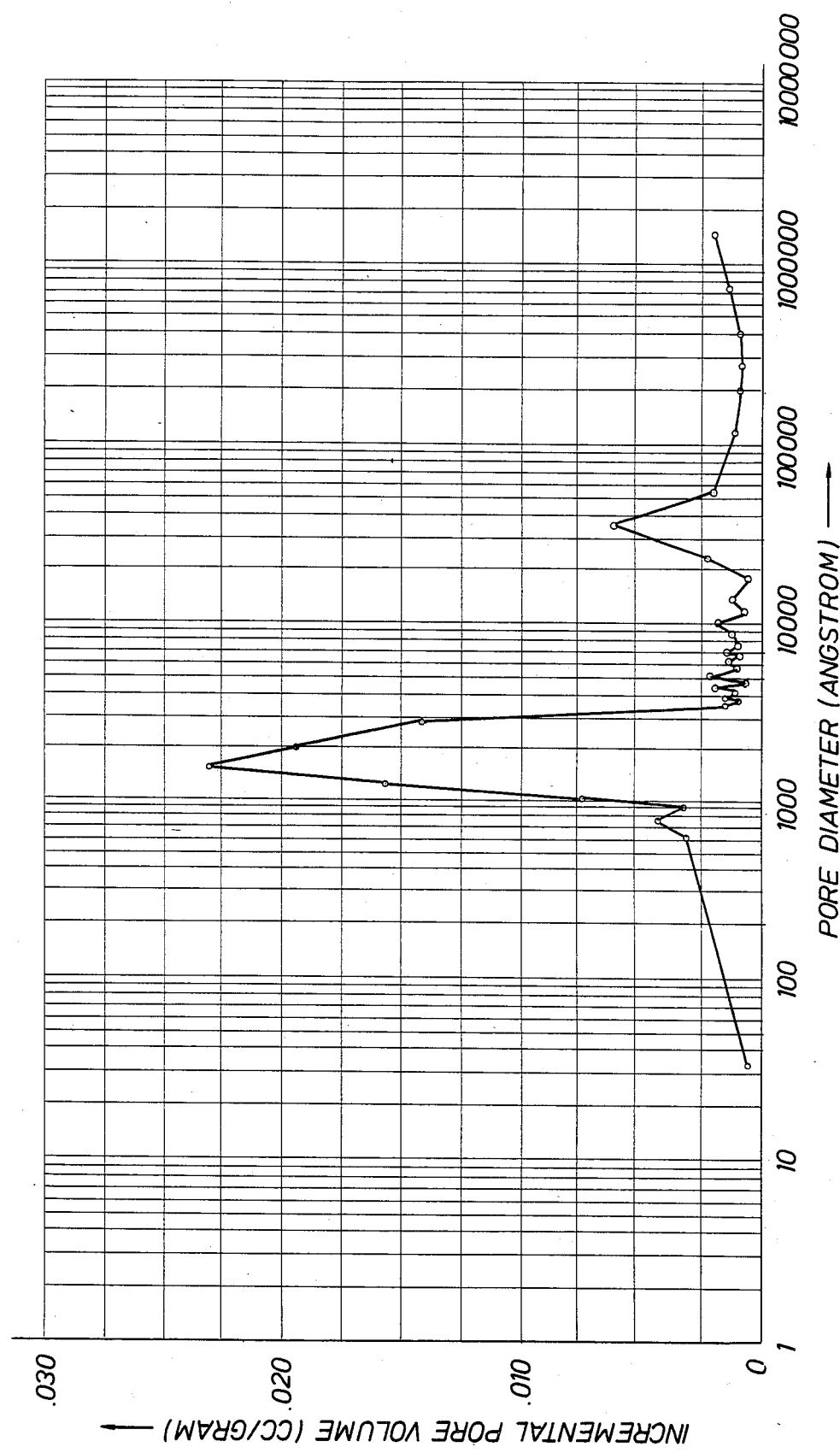
Figure 6:
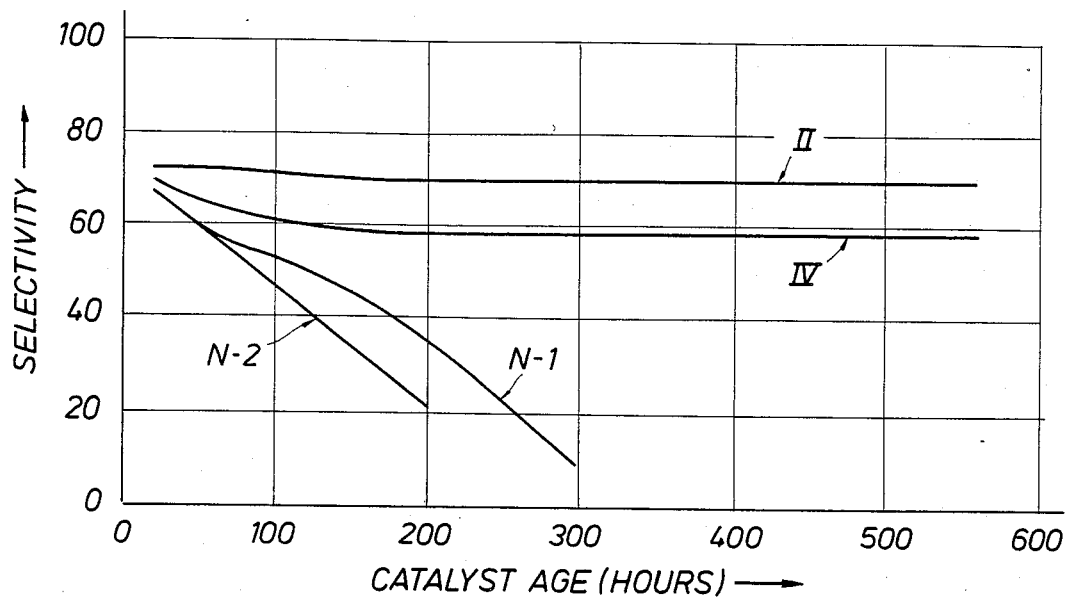
FIG. 6 illustrates selectivity (% of acetylene converted that shows up as ethylene make) as a function of catalyst age for palladium-chromium catalysts of the instant invention (II & IV) and palladium-chromium catalysts not according to the instant invention (N-1 and N-2).
Figure 7:
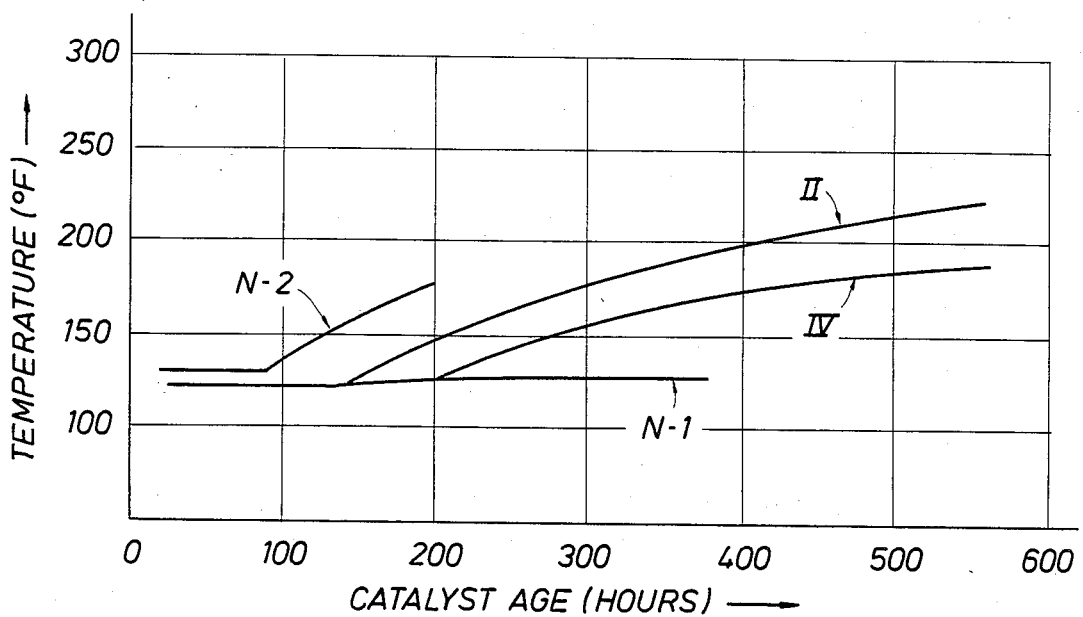
FIG. 7 illustrates activities for the same four catalysts.
Figure 8:
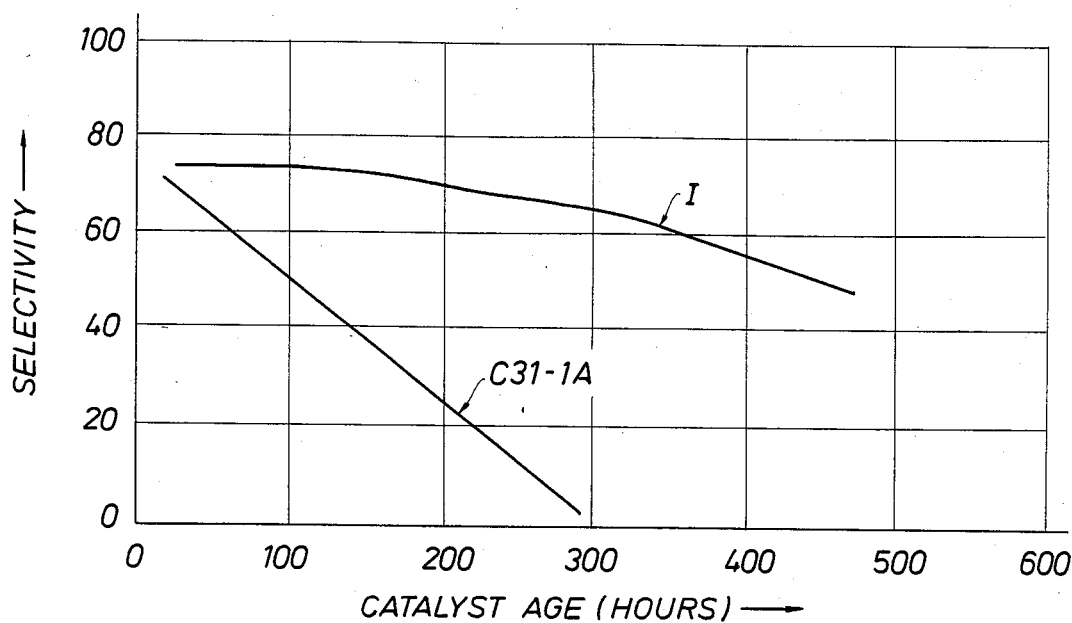
FIG. 8 illustrates selectivities for a palladium on alumina catalyst according to this invention (I) and a commercial palladium on alumina catalyst (C31-1A).
Figure 9:
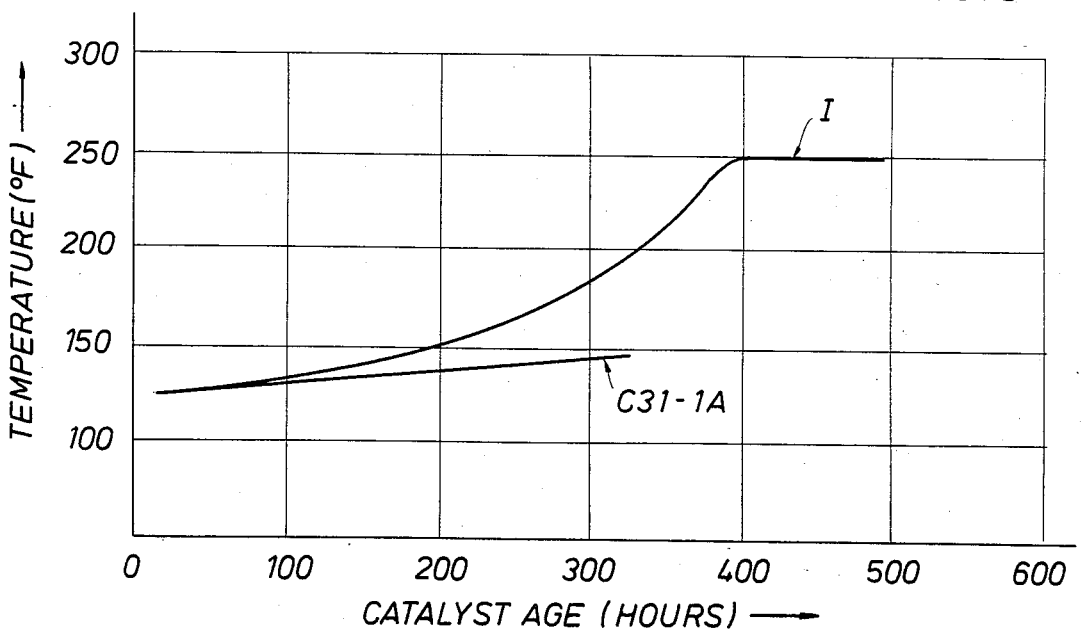
FIG. 9 illustrates activities for those catalysts noted in FIG. 8.

Example I–IV, N-1, N-2 and a commercial palladium on a alumina catalyst sold for the purpose of selective hydrogenation of acetylene in concentrated ethylene/ethane streams were tested according to the procedure described above. The commercial catalyst mentioned above is denoted C31-1A and is manufactured by United Catalysts, Inc. This commercial catalyst has those properties described in Table II above, and its pore volume characteristics are given in FIG. 5. The results for Examples II, IV, N-1 and N-2 are shown in FIGS. 6 and 7 and the results for Example I and the commercial catalyst C31-1A are shown in FIGS. 8 and 9.

I claim:
1. A process for the selective hydrogenation of acetylenic hydrocarbon impurities in a stream comprising lower olefins which comprises contacting at a temperature ranging from about 50° C. to about 200° C. said stream with hydrogen and a catalyst comprising palladium and optionally chromium supported on a porous carrier which comprises alumina having a surface area less than about 5 m²/g, a pore volume (Hg at 3000 psi) of between about 0.2 to about 0.5 cc/g and wherein greater than about 40% of the pore volume is contained in pores having pore diameters of greater than about 10 microns.

2. The process of claim 1 wherein the olefin is ethylene or propylene.

3. The process of claim 2 wherein the olefin is ethylene and the stream is in the gaseous state.

4. The process of claim 1 wherein the acetylenic hydrocarbon is acetylene.

5. The process of claim 4 wherein the concentration of acetylene is less than 2% by weight of the total gas stream.

6. The process of claim 5 wherein the molar ratio of hydrogen to acetylene is at least 1.

7. The process of claim 1 wherein the surface area of the carrier ranges from greater than about 0.5 to less than about 5 $m^2/g$.

8. The process of claim 7 wherein the surface area ranges from about about 1.5 to about 4.5.

9. The process of claim 1 wherein the carrier is at least about 90% by weight alumina.

10. The process of claim 1 wherein the catalyst contains palladium ranging from about 0.001 to about 5 percent by weight measured as the metal, of the total catalyst.

11. The process of claim 9 wherein the palladium ranges from about 0.01 to about 0.5.

12. The process of claim 1 wherein the catalyst contains chromium and the concentration of the palladium and chromium individually ranges from about 0.001 to about 5 percent by weight, measured as the metal, of the total catalyst.

13. The process of claim 12 wherein the concentration of the palladium and chromium individually ranges from about 0.01 to about 0.5.

14. The process of claim 1 wherein the median pore diameter ranges from about 0.5 to about 30 microns.

15. A process for the selective hydrogenation of acetylenic hydrocarbon impurities in a stream comprising lower olefins which comprises contacting at a temperature ranging from about 50° C. to about 200° C. said stream with hydrogen and a catalyst comprising palladium and optionally chromium supported on a porous carrier which comprises alumina having a surface area less than about 5 $m^2/g$, a pore volume (Hg at 3000 psi) of between about 0.2 to about 0.5 cc/g and wherein greater than about 50% of the pore volume is contained in pores having pore diameters of greater than 10 microns.

16. The process of claim 15 wherein the olefin is ethylene or propylene.

17. The process of claim 16 wherein the olefin is ethylene and the stream is in the gaseous state.

18. The process of claim 15 wherein the acetylenic hydrocarbon is acetylene.

19. The process of claim 18 wherein the concentration of acetylene is less than 2% by weight of the total gas stream.

20. The process of claim 19 wherein the molar ratio of hydrogen to acetylene is at least 1.

21. The process of claim 15 wherein the surface area of the carrier ranges from greater than about 0.5 to less than about 5 $m^2/g$.

22. The process of claim 21 wherein the surface area ranges from about 1.5 to about 4.5.

23. The process of claim 15 wherein the carrier is at least about 90% by weight alumina.

24. The process of claim 15 wherein the catalyst contains palladium ranging from about 0.001 to about 5 percent by weight measured as the metal, of the total catalyst.

25. The process of claim 24 wherein the palladium ranges from about 0.01 to about 0.5.

26. The process of claim 15 wherein the catalyst contains chromium and the concentration of the palladium and chromium individually ranges from about 0.001 to about 5 percent by weight, measured as the metal, of the total catalyst.

27. The process of claim 26 wherein the concentration of the palladium and chromium individually ranges from about 0.01 to about 0.5.

28. The process of claim 15 wherein the median pore diameter ranges from about 0.5 to about 30 microns.

* * * * *